US 6,724,188 B2

United States Patent
Butters et al.

(10) Patent No.: US 6,724,188 B2
(45) Date of Patent: Apr. 20, 2004

(54) APPARATUS AND METHOD FOR MEASURING MOLECULAR ELECTROMAGNETIC SIGNALS WITH A SQUID DEVICE AND STOCHASTIC RESONANCE TO MEASURE LOW-THRESHOLD SIGNALS

(75) Inventors: John T. Butters, Langley, WA (US); Bennett M. Butters, Lacey, WA (US); Lisa C. Butters, Langley, WA (US)

(73) Assignee: Wavbank, Inc., Seattle, WA (US)

( * ) Notice: Subject to any disclaimer, the term of this patent is extended or adjusted under 35 U.S.C. 154(b) by 0 days.

(21) Appl. No.: 10/112,927

(22) Filed: Mar. 29, 2002

(65) Prior Publication Data

US 2003/0184289 A1 Oct. 2, 2003

(51) Int. Cl.[7] .............................................. G01R 33/02
(52) U.S. Cl. ..................... 324/248; 324/239; 324/261
(58) Field of Search ................. 324/248, 239, 324/306, 117 R, 318, 266, 261, 262; 327/367, 328; 505/846, 845

(56) References Cited

U.S. PATENT DOCUMENTS

| | | | |
|---|---|---|---|
| 5,343,147 A | * | 8/1994 | Sager et al. ................. 324/239 |
| 5,458,142 A | | 10/1995 | Farmer et al. |
| 5,465,049 A | | 11/1995 | Matsuura et al. |
| 5,574,369 A | * | 11/1996 | Hibbs ........................... 324/248 |
| 5,656,937 A | | 8/1997 | Cantor |
| 5,789,961 A | * | 8/1998 | Bulsara et al. ............... 327/355 |
| 5,955,400 A | | 9/1999 | Yokosawa et al. |
| 6,020,782 A | | 2/2000 | Albert et al. |
| 6,136,541 A | | 10/2000 | Gulati |
| 6,142,681 A | | 11/2000 | Gulati |
| 6,285,249 B1 | | 9/2001 | Bulsara et al. |
| 6,320,369 B1 | | 11/2001 | Hidaka et al. |

FOREIGN PATENT DOCUMENTS

| | | |
|---|---|---|
| WO | WO 87/02981 A1 | 5/1987 |
| WO | WO 91/13611 A1 | 9/1991 |

(List continued on next page.)

OTHER PUBLICATIONS

Benveniste, J., "Molecular Signaling, What Is So Unacceptable for Ultra–Orthodox Scientists?" <http://www.digibio.com/cgi–bin/node.pl?nd=n5> and "From 'Water Memory' Effects to 'Digital Biology' . . . Understanding Digital Biology," <http://www.digibio.com/cgi–bin/node.pl?nd=n3> 1998.

Chapeau–Blondeau, F., "Input–Output Gains for Signal in Noise in Stochastic Resonance," *Physics Letters A* 232:41–48, 1997.

Chapeau–Blondeau, F., "Periodic and Aperiodic Stochastic Resonance with Output Signal–to–Noise Ratio Exceeding That at the Input," *International Journal of Bifurcation and Chaos* 9(1):267–272, 1999.

(List continued on next page.)

Primary Examiner—N. Le
Assistant Examiner—Subhash Zaveri
(74) Attorney, Agent, or Firm—Perkins Coie, LLP (57) ABSTRACT

An apparatus and method for the repeatable detection and recording of low-threshold molecular electromagnetic signals. The sample material and detection apparatus are contained with a magnetically shielded faraday cage to shield them from extraneous electromagnetic signals. The detection apparatus includes a detection coil and Super Conducting Quantum Interference Device ("SQUID"). White noise is injected external to the SQUID and the signals emitted by the sample material enhanced by stochastic resonance.

13 Claims, 6 Drawing Sheets

FOREIGN PATENT DOCUMENTS

| | | |
|---|---|---|
| WO | WO 91/14181 A1 | 9/1991 |
| WO | WO 94/17406 A1 | 8/1994 |
| WO | WO 99/54731 A1 | 10/1999 |
| WO | WO 00/01412 A1 | 1/2000 |
| WO | WO 00/17637 A1 | 3/2000 |
| WO | WO 00/17638 A1 | 3/2000 |

OTHER PUBLICATIONS

Kaufman, I., et al., "Zero–Dispersion Stochastic Resonance in a Model for a Superconducting Quantum Interference Device," *Physical Review E 57(1)*:78–87, 1998.

\* cited by examiner

APPARATUS AND METHOD FOR MEASURING MOLECULAR ELECTROMAGNETIC SIGNALS WITH A SQUID DEVICE AND STOCHASTIC RESONANCE TO MEASURE LOW-THRESHOLD SIGNALS

FIELD OF THE INVENTION

The present invention relates to an apparatus and method for detecting low-frequency molecular electromagnetic signals.

BACKGROUND OF THE INVENTION

It has recently become apparent that all molecules emit very low-threshold electromagnetic emissions, or signals. The detection of molecular electromagnetic signals opens up numerous opportunities in the fields of science, medicine and industry. For example, if the low-threshold molecular electromagnetic signal of a food contaminate could be detected during production and packaging, less reliable existing methods of detecting contamination could be eliminated. Another potential use of such molecular electromagnetic signals is the detection of substances within the human body, including, but not limited to, antigens, antibodies, parasites, viruses, abnormal cells, etc.

However, recognition of a particular electromagnetic signal first requires the measurement and categorization of such a signal. Existing apparatuses and methods for the detection of molecular electromagnetic signals do not detect a pure, repeatable signal. One known method for the detection and processing of electromagnetic signals is placing a sample substance in a shielded enclosure, subjecting the sample to electromagnetic excitation and detecting the excited signals with the use of a detection coil. This method results in a poor signal quality because of the relative lack of sensitivity of the apparatus and method used. In addition, excitation of the sample substance can result in a pattern of signals that are different than the electromagnetic signals of the substance in its natural state.

SUMMARY OF THE INVENTION

The present invention is directed to providing an apparatus and method for the repeatable detection and recording of low-threshold molecular electromagnetic signals. The present invention includes a magnetically shielded faraday cage to shield the sample material and detection apparatus from extraneous electromagnetic signals. The invention further includes within the magnetically shielded faraday cage a coil for injecting white or gaussian noise, a nonferrous tray to hold the sample, a gradiometer to detect the low-threshold molecular electromagnetic signals, a superconducting quantum interference device ("SQUID"), and a preamplifier.

The apparatus is used by placing a sample within the magnetically shielded faraday cage in close proximity to the noise coil and gradiometer. White noise is injected through the noise coil and modulated until the molecular electromagnetic signal is enhanced through stochastic resonance. The enhanced molecular electromagnetic signal, shielded from external interference by the faraday cage and the field generated by the noise coil, is then detected and measured by the gradiometer and SQUID. The signal is then amplified and transmitted to any appropriate recording or measuring equipment.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
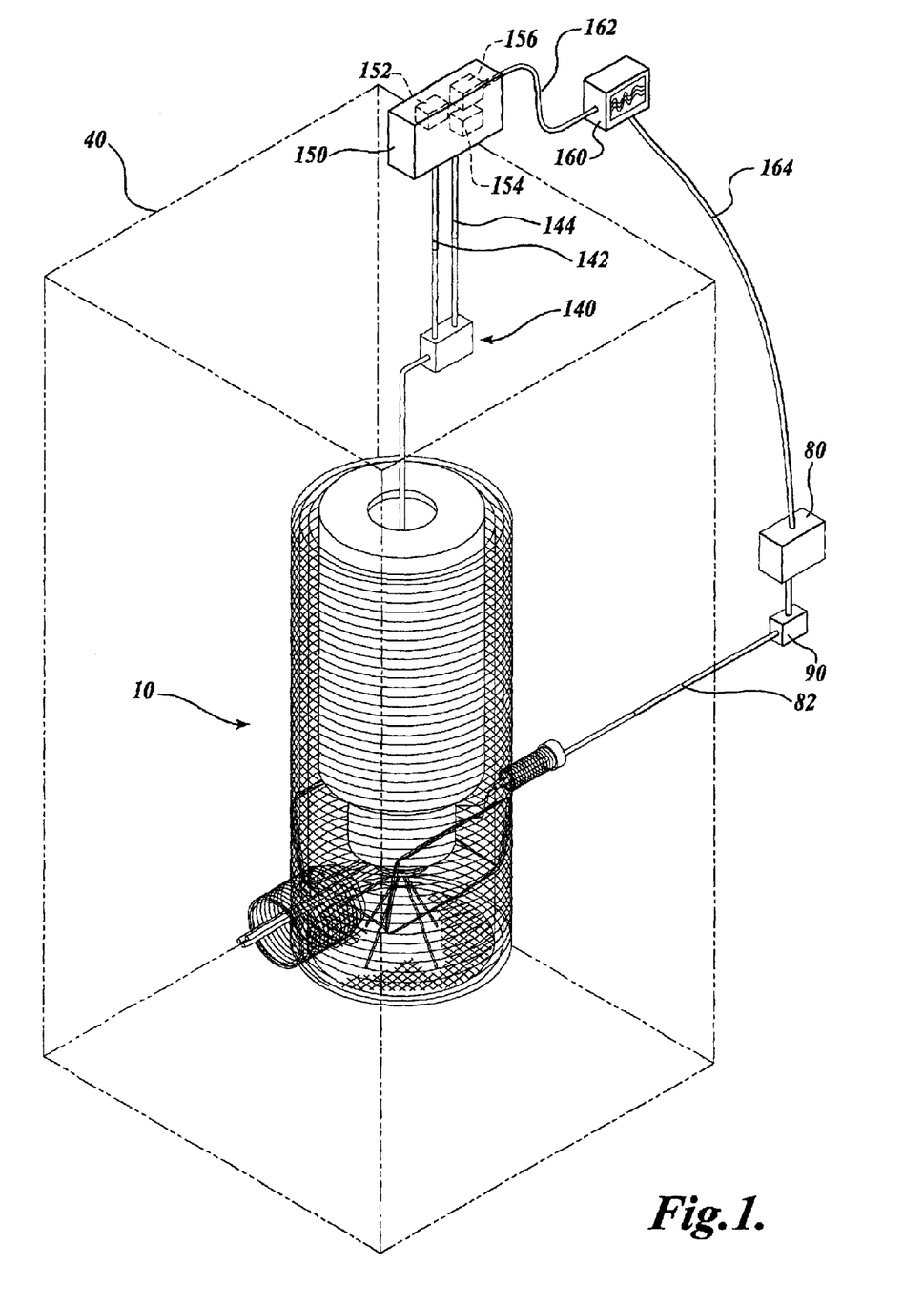
FIG. 1 is an isometric view of one embodiment of a molecular electromagnetic signaling detection apparatus formed in accordance with the present invention.
Figure 2:
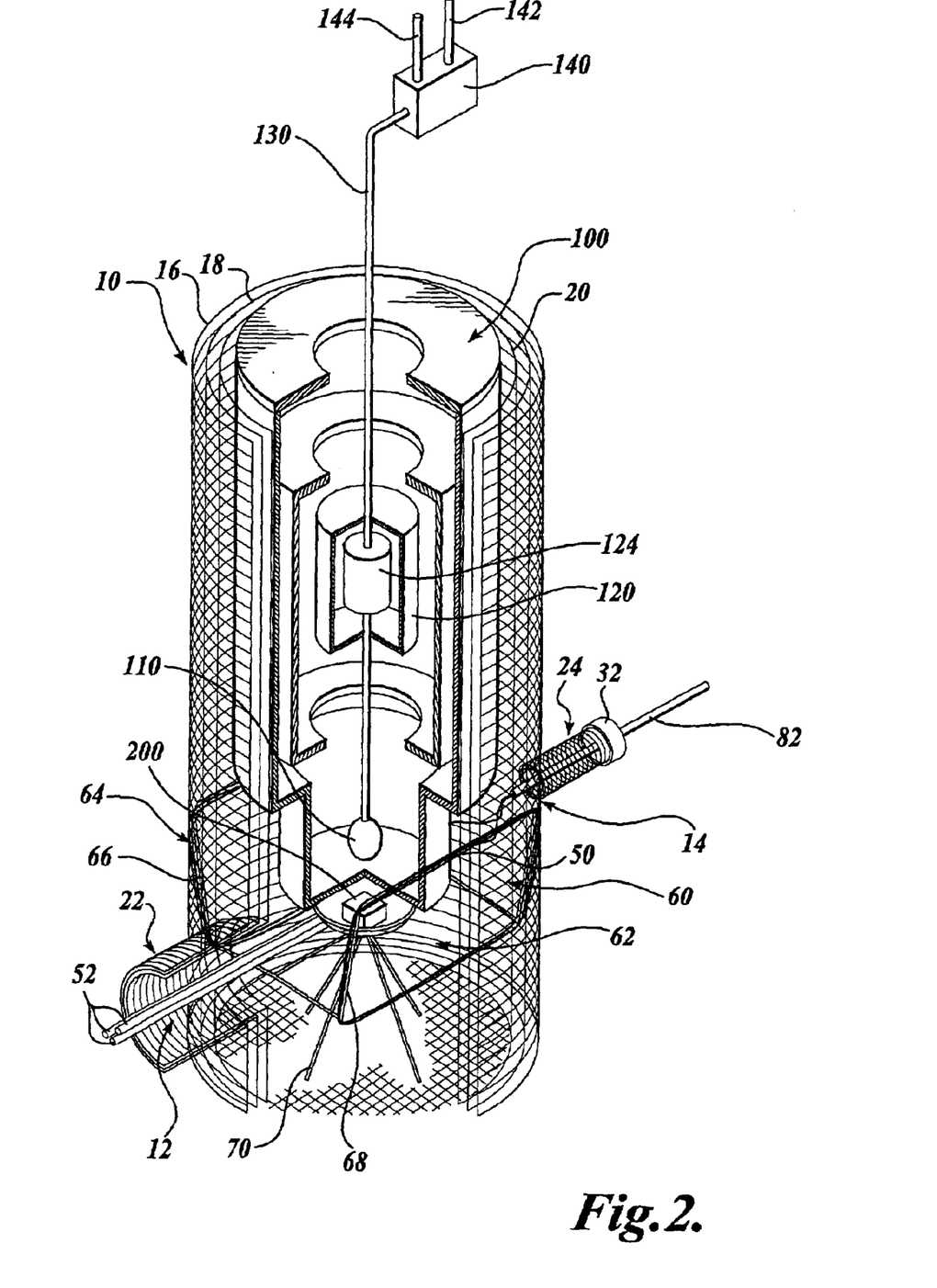
FIG. 2 is an enlarged, detail view of the faraday cage and its contents shown in FIG. 1.

Referring to FIG. 1, there is shown a faraday cage 10 contained within a larger magnetic shielding cage 40, which is further comprised of copper wire. Referring to FIG. 2, the faraday cage 10 is open at the top, and includes side openings 12 and 14. The faraday cage 10 is further comprised of three copper mesh cages 16, 18 and 20, nestled in one another. Each of the copper mesh cages 16, 18 and 20 is electrically isolated from the other cages by dielectric barriers (not shown) between each cage.

Figure 3:
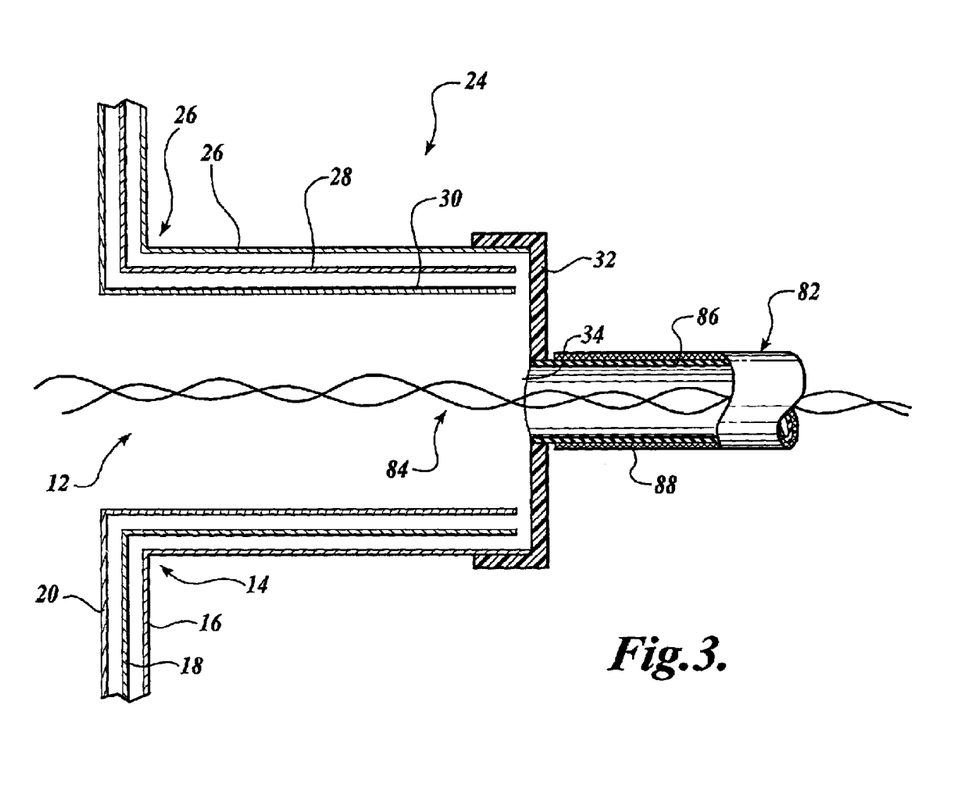
FIG. 3 is an enlarged, cross sectional view of one of the attenuation tubes shown in FIGS. 1 and 2.

Side openings 12 and 14 further comprise attenuation tubes 22 and 24 to provide access to the interior of the faraday cage 10 while isolating the interior of the cage from external sources of interference. Referring to FIG. 3, attenuation tube 24 is comprised of three copper mesh tubes 26, 28 and 30, nestled in one another. The exterior copper mesh cages 16, 18 and 20 are each electrically connected to one of the copper mesh tubes 26, 28 and 30, respectively. Attenuation tube 24 is further capped with cap 32, with the cap having hole 34. Attenuation tube 22 is similarly comprised of copper mesh tubes 26, 28 and 30, but does not include cap 32.

Referring again to FIG. 2, a low density nonferrous sample tray 50 is mounted in the interior of the faraday cage 10. The sample tray 50 is mounted so that it may be removed from the faraday cage 10 through the attenuation tube 22 and side opening 12. Three rods 52, each of which is greater in length than the distance from the center vertical axis of the faraday cage 10 to the outermost edge of the attenuation tube 22, are attached to the sample tray 50. The three rods 52 are adapted to conform to the interior curve of the attenuation tube 22, so that the sample tray 50 may be positioned in the center of the faraday cage 10 by resting the rods in the attenuation tube. In the illustrated embodiment, the sample tray 50 and rods 52 are made of glass fiber epoxy. It will be readily apparent to those skilled in the art that the sample tray 50 and rods 52 may be made of other nonferrous materials, and the tray may be mounted in the faraday cage 10 by other means.

Referring again to FIG. 2, mounted within the faraday cage 10 and above the sample tray 50 is a cryogenic dewar 100. In the disclosed embodiment, the dewar 100 is adapted to fit within the opening at the top of faraday cage 10 and is a Model BMD-6 Liquid Helium Dewar manufactured by Tristan Technologies, Inc. The dewar 100 is constructed of a glass-fiber epoxy composite. A gradiometer 110 with a very narrow field of view is mounted within the dewar 100 in position so that its field of view encompasses the sample tray 50. In the illustrated embodiment, the gradiometer 110 is a first order axial detection coil, nominally 1 centimeter in diameter, with a 2% balance, and is formed from a superconductor. The gradiometer can be any form of gradiometer excluding a planar gradiometer. The gradiometer 110 is connected to the input coil of one low temperature direct current superconducting quantum interference device ("SQUID") 120. In the disclosed embodiment, the SQUID is a Model LSQ/20 LTS dc SQUID manufactured by Tristan Technologies, Inc. It will be recognized by those skilled in the art that high temperature or alternating current SQUIDs can be used without departing from the spirit and scope of the invention. In an alternative embodiment, the SQUID 120 includes a noise suppression coil 124.

The disclosed combination of gradiometer 110 and SQUID 120 have a sensitivity of 20 microTesla/√Hz when measuring magnetic fields.

The output of SQUID 120 is connected to a Model SP Cryogenic Cable 130 manufactured by Tristan Technologies, Inc. The Cryogenic Cable 130 is capable of withstanding the temperatures within and without the dewar 100 and transfers the signal from the SQUID 120 to Flux-Locked Loop 140, which is mounted externally to the faraday cage 10 and dewar 100. The Flux-Locked Loop 140 in the disclosed embodiment is an iFL-301-L Flux Locked Loop manufactured by Tristan Technologies, Inc.

Referring to FIG. 1, the Flux Locked Loop 140 further amplifies and outputs the signal received from the SQUID 120 via high-level output circuit 142 to an iMC-303 iMAG® SQUID controller 150. The Flux-Locked Loop 140 is also connected via a model CC-60 six meter fiber-optic composite connecting cable 144 to the SQUID controller 150. The fiber-optic connecting cable 144 and SQUID controller 150 are manufactured by Tristan Technologies, Inc. The controller 150 is mounted externally to the magnetic shielding cage 40. The fiber-optic connecting cable 144 carriers control signals from the SQUID controller 150 to the Flux Locked Loop 140, further reducing the possibility of electromagnetic interference with the signal to be measured. It will be apparent to those skilled in the art that other Flux-Locked Loops, connecting cables, and Squid controllers can be used without departing from the spirit and scope of the invention.

The SQUID controller 150 further comprises high resolution analog to digital converters 152, a standard GP-IB bus 154 to output digitalized signals, and BNC connectors 156 to output analog signals. In the illustrated embodiment, the BNC connectors are connected to a dual trace oscilloscope 160 through patch cord 162.

Referring to FIG. 2, a two-element Helmholtz transformer 60 is installed to either side of the sample tray 50 when the sample tray is fully inserted within the faraday cage 10. In the illustrated embodiment, the coil windings 62 and 64 of the Helmholtz transformer 60 are designed to operate in the direct current to 50 kilohertz range, with a center frequency of 25 kilohertz and self-resonant frequency of 8.8 megahertz. In the illustrated embodiment, the coil windings 62 and 64 are generally rectangular in shape and are approximately 8 inches tall by 4 inches wide. Other Helmholtz coil shapes may be used but should be shaped and sized so that the gradiometer 110 and sample tray 50 are positioned within the field produced by the Helmholtz coil. Each of coil windings 62 and 64 is mounted on one of two low density nonferrous frames 66 and 68. The frames 66 and 68 are hingedly connected to one another and are supported by legs 70. Frames 66 and 68 are slidably attached to legs 70 to permit vertical movement of the frames in relation to the lower portion of dewar 100. Movement of the frames permits adjustment of the coil windings 62 and 64 of the Helmholtz transformer 60 to vary the amplitude of white noise received at gradiometer 110. The legs 70 rest on or are epoxied onto the bottom of the faraday cage 10. In the illustrated embodiment, the frames 66 and 68 and legs 70 are made of glass fiber epoxy. Other arrangements of transformers or coils may be used around the sample tray 50 without departing from the spirit and scope of the invention.

Figure 4:
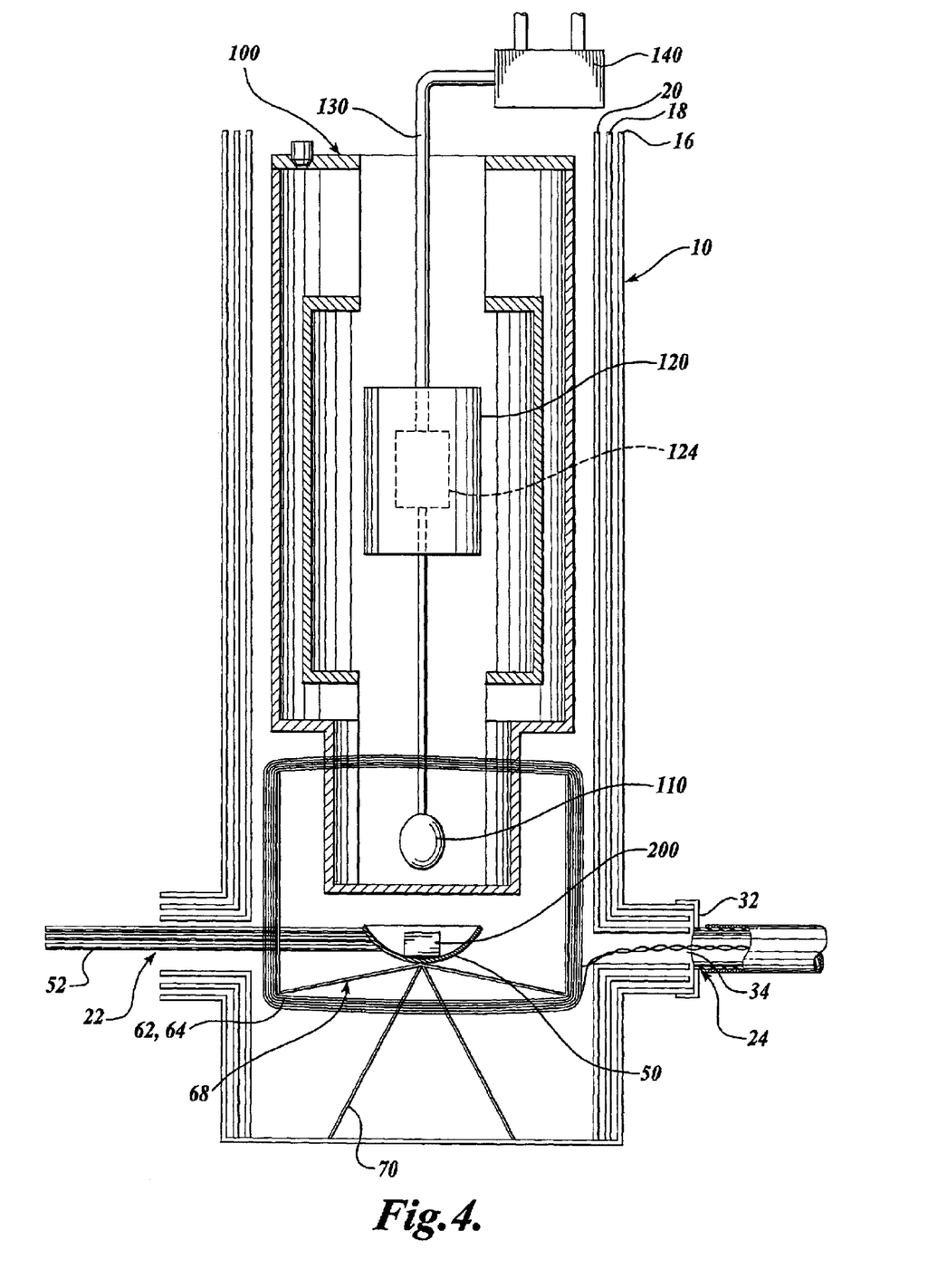
FIG. 4 is a cross-section view of the faraday cage and its contents shown in FIG. 2.

Referring to FIG. 4, there is shown a cross-sectional view of the faraday cage and its contents, showing windings 62 of Helmholtz transformer 60 in relation to dewar 100 and faraday cage 10. Note also in FIG. 4 the positioning of sample tray 50 and sample 200.

Figure 5:
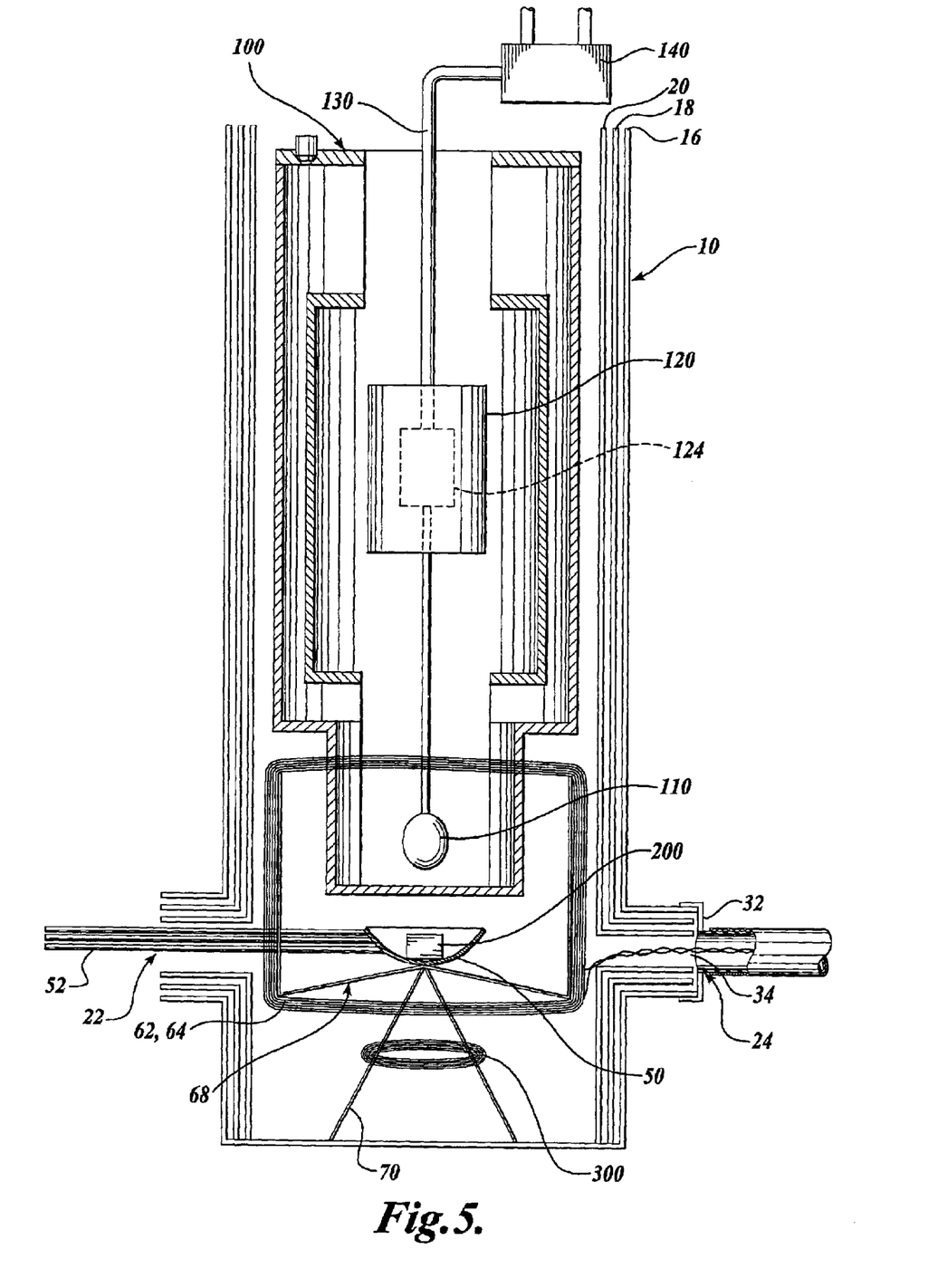
FIG. 5 is a cross-section view of an alternative embodiment of the invention shown in FIGS. 1 through 4.

Referring to FIG. 5, there is shown an alternative embodiment in which the Helmholtz coil windings 62 and 64 are fixed in a vertical orientation and an additional noise coil 300 is positioned below sample tray 50. The windings of the additional noise coil 300 are substantially perpendicular to the vertical windings 62 and 64 of Helmholtz transformer 60, and the windings of the additional noise coil 300 are thus substantially in parallel orientation to the bottom of faraday cage 10.

In this alternative embodiment, noise would be fed to noise coil 300 from an identical twisted pair wire (not shown) as that supplying the Helmholtz coil. The noise source would originate with the same noise generator used to supply noise to the Helmholtz coil. Noise would be sampled either at the noise generator via an additional noise output connection, or via a balanced splitter from an output connection to the noise generator. Attenuation of the noise signal at additional noise coil 300 would be through an adjustable RF signal attenuation circuit, of which many are available commercially, or via a suitable series of fixed value RF attenuation filters.

Figure 6:
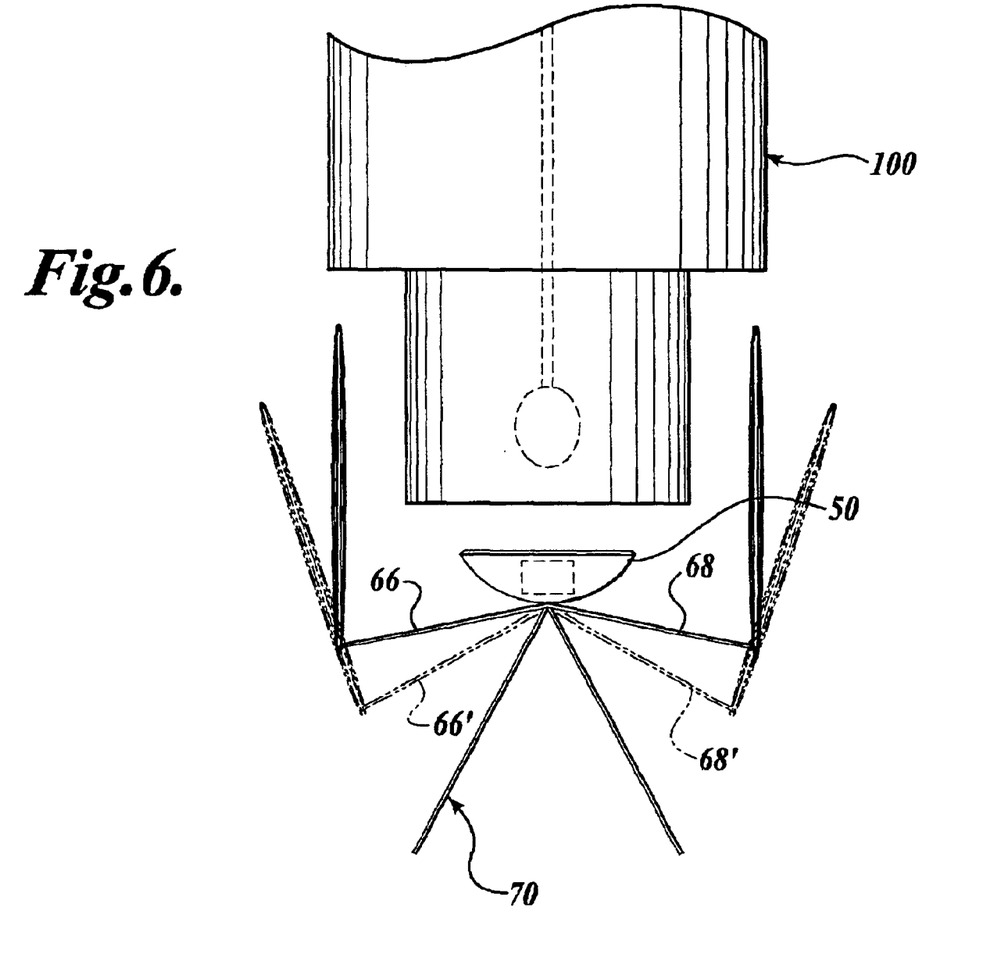
FIG. 6 is an enlarged, detail view of the frames supporting the coils of the Helmholtz transformer described herein.

Referring to FIG. 6, a detail of the frames supporting the coils of Helmholtz transformer 60 may be seen; the reference point of FIG. 6 is 90 degrees from the view of FIG. 4, and omits the faraday cage 10. Frames 66 and 68 are disposed to show the coil windings of the Helmholtz coil in a substantially vertical position and parallel to one another. Frames 66' and 68' illustrate the rotation of said frames about the axis of the hinged connection joining said frames, so as to dispose the coil windings of the Helmholtz transformer in an non-parallel relationship with one another.

Referring again to FIG. 1, an amplitude adjustable white noise generator 80 is external to magnetic shielding cage 40, and is electrically connected to the Helmholtz transformer 60 through filter 90 by electrical cable 82. Referring to FIG. 3, cable 82 is run through side opening 12, attenuation tube 24, and through cap 32 via hole 34. Cable 82 is a co-axial cable further comprising a twisted pair of copper conductors 84 surrounded by interior and exterior magnetic shielding 86 and 88, respectively. In other embodiments, the conductors can be any nonmagnetic electrically conductive material, such as silver or gold. The interior and exterior magnetic shielding 86 and 88 terminates at cap 32, leaving the twisted pair 84 to span the remaining distance from the end cap to the Helmholtz transformer 60 shown in FIG. 1. The interior magnetic shielding 86 is electrically connected to the exterior copper mesh cage 16 through cap 32, while the exterior magnetic shielding is electrically connected to the magnetically shielded cage 40 shown in FIG. 1.

Referring to FIG. 1, the white noise generator 80 can generate nearly uniform noise across a frequency spectrum from zero to 100 kilohertz. In the illustrated embodiment, the filter 90 filters out noise above 50 kilohertz, but other frequency ranges may be used without departing from the spirit and scope of the invention.

White noise generator 80 is also electrically connected to the other input of dual trace oscilloscope 160 through patch cord 164.

Referring to FIGS. 1, 2 and 3, a sample of the substance 200 to be measured is placed on the sample tray 50 and the sample tray is placed within the faraday cage 10. In the first embodiment, the white noise generator 80 is used to inject white noise through the Helmholtz transformer 60. The noise signal creates an induced voltage in the gradiometer 110. The induced voltage in the gradiometer 110 is then detected and amplified by the SQUID 120, the output from the SQUID is further amplified by the flux locked loop 140 and sent to the SQUID controller 150, and then sent to the dual trace oscilloscope 160. The dual trace oscilloscope 160 is also used to display the signal generated by white noise generator 80.

The white noise signal is adjusted by altering the output of the white noise generator 80 and by rotating the Helmholtz transformer 60 around the sample 200, shown in FIG. 2. Rotation of the Helmholtz transformer 60 about the axis of the hinged connection of frames 66 and 68 alters its phasing with respect to the gradiometer 110. Depending upon the desired phase alteration, the hinged connection of frames 66 and 68 permits windings 62 and 64 to remain parallel to one another while rotating approximately 30 to 40 degrees around sample tray 50. The hinged connection also permits windings 62 and 64 to rotate as much as approximately 60 degrees out of parallel, in order to alter signal phasing of the field generated by Helmholtz transformer 60 with respect to gradiometer 110. The typical adjustment of phase will include this out-of-parallel orientation, although the other orientation may be preferred in certain circumstances, to accommodate an irregularly-shaped sample 200, for example. Noise is applied and adjusted until the noise is 30 to 35 decibels above the molecular electromagnetic emissions sought to be detected. At this noise level, the noise takes on the characteristics of the molecular electromagnetic signal through the well known phenomenon of stochastic resonance. The stochastic product sought is observed when the oscilloscope trace reflecting the signal detected by gradiometer 110 varies from the trace reflecting the signal directly from white noise generator 80. In alternative embodiments, the signal can be recorded and or processed by any commercially available equipment.

In an alternative embodiment, the method of detecting the molecular electromagnetic signals further comprises injecting noise 180° out of phase with the original noise signal applied at the Helmholtz transformer 60 through the noise suppression coil 124 of the SQUID 120. The stochastic product sought can then be observed when the oscilloscope trace reflecting the signal detected by gradiometer 110 becomes non-random.

Regardless of how the noise is injected and adjusted, the stochastic product can also be determined by observing when an increase in spectral peaks occurs. The spectral peaks can be observed as either a line plot on oscilloscope 160 or as numerical values, or by other well known measuring devices.

The present invention provides a method and apparatus for detecting extremely low-threshold molecular electromagnetic signals without external interference. The present invention further provides for the output of those signals in a format readily usable by a wide variety of signal recording and processing equipment.

While the preferred embodiment of the invention has been illustrated and described, it will be appreciated that various changes can be made therein without departing from the spirit and scope of the invention.

What is claimed is:

1. An apparatus for detecting molecular signals from a sample, the apparatus comprising:
 (a) a magnetic shielding cage positioned outside of a cryogenic container;
 (b) a faraday cage contained within the magnetic shielding cage positioned outside of a cryogenic container;
 (c) a electromagnetic emission detection coil contained within the faraday cage and positioned near to the sample to detect molecular signals from the sample as combined with white noise;
 (d) a Super Conducting Quantum Interference Device contained within the faraday cage and cryogenic container, and electrically connected to the electromagnetic emission detection coil;
 (e) a Super Conducting Quantum Interference Device controller external to the magnetic shielding cage and connected to the Super Conducting Quantum Interference Device;
 (f) an amplitude adjustable white noise generator exterior to the magnetic shielding cage and producing the white noise signal over multiple frequencies;
 (g) a noise coil contained within the faraday cage and electrically connected to the white noise generator to output the white noise signal over the multiple frequencies; and
 (h) a dual trace oscilloscope external to the magnetic shielding cage and electrically connected to the Super Conducting Quantum Interference Device controller and the white noise generator.

2. The apparatus of claim 1, wherein the electromagnetic emission detection coil is a gradiometer.

3. The apparatus of claim 1, wherein the noise coil is a two-element Helmholtz coil.

4. The apparatus of claim 3, wherein the two-element Helmholtz coil is rotatably mounted within the faraday cage.

5. The apparatus of claim 1, wherein the Super Conducting Quantum Interference Device further comprises a noise suppression coil.

6. The apparatus of claim 1, further comprising a low pass filter electrically connected between the white noise generator and the noise coil and external to the magnetic shielding cage.

7. The apparatus of claim 1, wherein the Super Conducting Quantum Interference Device is electrically connected to a flux locked loop and the flux locked loop is electrically and optically connected to the Super Conducting Quantum Interference Device controller, the flux locked loop being external to the faraday cage and within the magnetic shielding cage.

8. An apparatus for detecting molecular signals from a sample, the apparatus comprising:
 (a) a magnetic shielding cage positioned outside of a cryogenic dewar;
 (b) a faraday cage contained within the magnetic shielding cage;
 (c) a gradiometer contained within the faraday cage and positioned near a holder for holding the sample to detect molecular signals from the sample as combined with white noise;

(d) a Super Conducting Quantum Interference Device contained within the faraday cage and within the cryogenic dewar, and electrically connected to the gradiometer, the Super Conducting Quantum Interference Device further comprising a noise suppression coil;

(e) a flux locked loop external to the faraday cage and internal to the magnetic shielding cage and electrically connected to the Super Conducting Quantum Interference Device;

(f) a Super Conducting Quantum Interference Device controller external to the magnetic shielding cage and electrically and optically connected to the flux locked loop;

(g) an amplitude adjustable white noise generator exferior to the magnetic shielding cage and configured to produce the white noise;

(h) a filter exterior to the magnetic shielding cage and electrically connected to the amplitude adjustable white noise generator;

(i) a two element Helmholtz coil rotatably mounted within the faraday cage and electrically connected to the filter and (h) a dual trace oscilloscope external to the magnetic shielding cage and electrically connected to the Super Conducting Quantum Interference Device controller and the white noise generator.

9. An apparatus for detecting molecular signals from a sample, the apparatus comprising:

(a) a signal source from the sample;

(b) an electromagnetic emission detection coil positioned near to the sample;

(c) a Super Conducting Quantum Interference Device electrically connected to the electromagnetic emission detection coil, wherein the Super Conducting Quantum Interference Device is positioned within a means for cryogenically cooling;

(d) means for surrounding the signal source and the means for detecting signals with white noise, wherein the white noise has a substantially uniform amplitude over multiple frequencies;

(e) means for electromagnetically shielding the signal source, electromagnetic emission detection coil, Super Conducting Quantum Interference Device, and white noise means from external electromagnetic radiation, and wherein the means for electromagnetically shielding is positioned exterior to the means for cryogenically cooling;

(f) means for controlling the Super Conducting Quantum Interference Device; and (g) means for observing the signal detected by the electromagnetic emission detection coil.

10. A method for detecting molecular signals from a sample, the method comprising:

(a) inserting the sample a into a magnetically shielded detection apparatus, wherein the sample acts as a signal source for molecular signals, and wherein the magnetically shielded detection apparatus includes a cryogenic container and magnetic shielding external to the cryogenic container;

(b) injecting noise into the magnetically shielded detection apparatus in the absence of another generated signal from another signal source, wherein the noise has a substantially uniform amplitude over a plurality of frequencies;

(c) detecting a combination of the noise and the signal emitted by the signal source in the cryogenic container and in the substantial absence of the another generated signal from another signal source;

(d) observing the combination; and (e) adjusting the noise until the combination takes on the characteristic of the signal generated by the signal source through stochastic resonance.

11. A method for detecting molecular signals from a sample, wherein the sample produces low amplitude signals, the method comprising:

(a) inserting the sample, as a signal sources into a magnetically shielded detection apparatus to provide the low amplitude signals;

(b) injecting noise into the magnetically shielded detection apparatus by way of a Helmholtz coil, wherein the noise has a substantially uniform amplitude over a plurality of frequencies;

(c) detecting a combination of the noise and the signal from the sample signal source;

(d) injecting noise 180° out of phase with the noise injected into the magnetically shielded detection apparatus into the combination by way of a noise suppression coil;

(e) observing the output of the combination of said the sample signal source, noise injected into the magnetically shielded detection apparatus, and the out of phase noise; and (e) adjusting the noise until the output becomes nonrandom.

12. A method for detecting molecular signals from a sample, the method comprising:

(a) inserting the samples into a magnetically shielded detection apparatus to provide molecular signals;

(b) injecting white noise into the magnetically shielded detection apparatus;

(c) detecting a combination of the white noise and the signal emitted by the signal source by way of a first order gradiometer having a signal sensing coil, and a noise cancellation coil;

(d) comparing the combination with the white noise; and (e) adjusting an amplitude of the white noise until the combination takes on a different characteristic than the noise through stochastic resonance.

13. The apparatus of claim 8, wherein the two elements of the Helmholtz coil are pivotable with respect to each other.

* * * * *

UNITED STATES PATENT AND TRADEMARK OFFICE
CERTIFICATE OF CORRECTION

PATENT NO. : 6,724,188 B2
DATED : April 20, 2004
INVENTOR(S) : John T. Butters et al.

It is certified that error appears in the above-identified patent and that said Letters Patent is hereby corrected as shown below:

Column 7,
Line 15, "exferior" should be -- exterior --;
Line 22, insert semicolon between "filter" and "and";
Line 55, delete "a" between "sample" and "into";

Column 8,
Line 20, "sources" should be -- source --;
Line 46, "signal source" should be -- sample --;

Signed and Sealed this

Eighth Day of February, 2005

JON W. DUDAS
*Director of the United States Patent and Trademark Office*